United States Patent [19]
Faisandier

[11] Patent Number: 5,623,935
[45] Date of Patent: Apr. 29, 1997

[54] DATA COMPRESSION METHODS AND APPARATUS FOR USE WITH PHYSIOLOGICAL DATA

[75] Inventor: Yves Faisandier, Paris, France

[73] Assignee: Ela Medical, S.A., Montrouge, France

[21] Appl. No.: 499,438

[22] Filed: Jul. 7, 1995

[30] Foreign Application Priority Data

Jul. 7, 1994 [FR] France .................................. 94 08406

[51] Int. Cl.$^6$ ........................................................ A61B 5/04
[52] U.S. Cl. .............................................................. 128/696
[58] Field of Search ..................................... 728/630, 696; 364/413.02, 413.06, 715.02

[56] References Cited

FOREIGN PATENT DOCUMENTS 0129981 5/1984 European Pat. Off. ......... G06F 15/20
0552009 1/1993 European Pat. Off. ......... G06F 15/20

OTHER PUBLICATIONS

S.C. Tai, Slope–a real–time ECG data compressor, Medical & Biological Engineering And Computing, vol. 29, pp. 175–176, Mar. 1991.
Lin Jun, Full Use Of Memory for 12bit ADC data acquisition, Electronic Engineering, vol. 63, No. 780, London, p. 30, Dec. 1991.
G. Passariello et al., Arithmetic Coding for ECG Data Compression, Proceedings Of Computers In Cardiology IEEE Press New York, pp. 593–596, Sep. 23, 1991.
Peng–Wie Hsia, Ph.D., Electrocardiographic Data Compression Using Preceding Consecutive QRS Information, Proceedings Of Computers In Cardiology, IEEE Press New York US, pp. 465–468, Sep. 25, 1988, Washington, U.S.
P.J. Narramore, et al., Optimising Solid State Holter Systems, Proceedings of Computers In Cardiology, IEEE Press New York US, pp. 575–578, Sep. 25, 1988, Washington U.S.

*Primary Examiner*—William E. Kamm
*Attorney, Agent, or Firm*—Orrick, Herrington & Sutcliffe LLP

[57] ABSTRACT

A process of physiological data compression, notably cardiac activity, especially for a recording of an electrocardiogram or a Holter electrogram. This process is characterized by the following successive operations: (a) acquisition of data by collection of an electrical signal and sampling of this signal at a given frequency; (b) determination of the first derivative of the sampled signal; (c) determination of the second derivative of the sampled signal; (d) analyze predictively the sampled signal according to a plurality of values of first and second derivatives and selection, for the current sample, of a mode of coding from among a plurality of predetermined coding modes which are commutable dynamically, in a manner to optimize the global code volume created for coding the aforementioned plurality of future values; and (e) compression of data by the implementation of the coding mode chosen at stage (d). Decompression occurs by the inverse of the compression mode of coding. An apparatus for performing the compression in a Holter recording device is described.

22 Claims, 2 Drawing Sheets

DATA COMPRESSION METHODS AND APPARATUS FOR USE WITH PHYSIOLOGICAL DATA

FIELD OF THE INVENTION

The invention concerns the compression of physiological data, more particularly signals indicative of cardiac activity. The invention is particularly adapted to compress so-called "Holter" recordings, that is to say to signal recordings collected continuously and over a long period of time by implanted electrodes ("electrogram") or external electrodes ("electrocardiogram").

The data compression of the present invention also is applicable to other types of physiological data, such as respiratory activity and rhythms, blood pressure, etc., as well as nonphysiological data. Although the following description refers mainly to the compression of Holter recordings of electrocardiograms (ECG), which constitutes a frequent application, the invention is not restricted to such an application. Indeed, the present invention is perfectly suited to the compression of data produced by implanted machines, such as (in the cases of cardiac activity and Holter data) implanted pacemakers, cardiovertors or defibrillators. In addition, the present invention is applicable to the compression of sensed data, during acquisition, in view of recording the compressed data in one of these implanted machines, as well as during the transmission to an exterior device, such as a programmer/analyzer, of at least some portion of the information already recorded in the implanted machine. In this regard, the inventors have recognized that it can indeed be desirable to compress the sensed data to be transmitted (whether or not the compressed data is recorded) to limit the time of transmission of information to an external programmer, considering the slow speed of the flow of information, which is limited by the relatively narrow usable band width of the known implanted-external transmission systems.

BACKGROUND OF THE INVENTION

Holter recordings are in common usage recorded on magnetic tape in view of the volume of information to memorize, i.e., to record or store in a memory. More recently, these recordings are, increasingly stored in a static semi-conductor memory device, a so-called "Holter memory". The utilization of this technology is however limited by the lesser capacity of static memories as compared to magnetic tapes, which obliges, at the moment of the acquisition of data and before recording the acquired data in memory, to use a compression algorithm to economize use of the available storage capacity in the Holter memory.

Thus, if one wants to record during a 24 hour period the ECG signals collected on two channels (leads) and if the ECG signal on each channel is sampled at 100 Hz with a resolution of 10 μV and a dynamic range of 10 mV, the flow of information on each ECG channel is 1000 bits/second (100 words of 10 bits each). If, for example, one has static memories allowing a capacity of Holter memory of 10 Megabytes (MB), on which one reserves 1 MB for files of analysis results, histogram, etc., there remains 4.5 MB available to memorize the 24 hours of signals of each of channel. This constraint of size imposes a serious limitation on the flow of data to memorize 52.08 bytes/second, corresponding to 422.4 bits/second; it is therefore necessary to compress data by a factor of at least 1000/422.4=2.36.

For a signal having more detailed information, and where higher resolution is appropriate, the processor can sample (digitize) the ECG signals at a higher sampling frequency, 200 Hz, for example. All other things being equal in such a case, the rate of compression has then to increase to 4.72.

Heretofore, a number of processes have been proposed to compress physiological data such as Holter information. The particular problems posed by the ambulatory recorded ECG are its irregularity and the presence of many artifacts. The ECG signal typically is constituted by the cardiac origin signal, which is almost periodic (the PQRST complex), accompanied by signals generated by muscles, by mechanical perturbations of the electrode—skin interface, and by electrical perturbations such as electromagnetic interference captured by the cables connecting electrodes to the recorder.

Classic algorithms appear to be relatively effective in the particular case of regular ECG signals. However, concerning signals that are affected with significant parasitic signals, the classic algorithms are inadequate to eliminate the parasites.

On the other hand, it is important that the data compression/decompression sequence does not introduce artifacts that are too visible. Such artifacts occur, for example, in the case of the known compressions using approximations by parabolic or right segment arcs. Such artifacts introduce to the display screen waveform "breakages" that are very visible to the eye. These breakages are susceptible to impair the interpretation of the ECG waveform trace by the therapist. In this regard, a reconstructed displayed ECG trace may have an appearance that is similar to a different "normal" tracing, and the therapist may incorrectly interpret the reconstructed displayed trace with its breakages as the normal ECG without realizing the error.

In addition, in the case of an ECG signal, it is important that one may observe the variability of the QRS complex, which can be very significant for the diagnosis, and therefore one must be able to preserve a certain number of microvariations.

This constraint renders, in practice, an inefficient predictive compression algorithm, based on the repetition of an average signal (the PQRST complex), because the multitude of forms of different PQRST complexes renders their operation very difficult and their performance degrades rapidly. The compression algorithm not only has to function in the ideal case, that is to say for a regular ECG and without parasitic signals, but it also must be able to support very irregular ECGs (frequent abnormal complexes, of a form very variable, for example, with stable periods), some of which contain artifacts.

Another typical difficulty in recording Holter data is the fact that machines have to be able to function autonomously on batteries for 24 and sometimes 48 hours. Now, the utilization of a complex algorithm necessitates a sufficiently powerful processor functioning more or less continuously. This implies a large energy consumption and a limitation of the duration of recording, to minimize the weight and the size of the machine.

OBJECTS AND SUMMARY OF THE INVENTION

It is, therefore, an object of the invention to propose a new process of compressing physiological data that is particularly well adapted to the constraints of Holter recordings, among which are: the detection and storage of a signal very irregular in time; the presence of many parasitic signals and artifacts that will not result in a degradation of the useful signal due to the fact of the compression; the limited memory capacity of current static mass memories, and, therefore, the necessity to compress data with a high compression rate without appreciably degrading the memorized compressed data information; and the limited energy supply of these autonomous machines, that imposes the choice of a rapid algorithm so as to reduce as much as possible the rate of utilization of the processor, and therefore its global energy consumption.

To reach these goals, the present invention broadly proposes a process characterized by a sequence of successive stages: (a) data acquisition by collection of an electrical signal in a conventional manner and sampling of this signal at a given sampling frequency; (c) determination of the first derivative of the sampled signal; (e) determination of the second derivative of this same sampled signal; (f) predictive analysis of the sampled signal as a function of a plurality of values of the first and second derivatives, and selection, for the current sample, of a mode of coding from among a plurality of predetermined coding modes, which modes are commutable dynamically, in a manner to optimize the global code volume created for the aforementioned coding of the plurality of future values; and (g) compression of data by implementation of the chosen mode of coding. The compressed data may then be stored or transmitted to a different device, as described further below.

The step (f) of predictive analysis is a process that uses recently obtained data to select a coding mode that will minimize the number of bits needed to represent the compressed data (for storage in a static memory or for transmission). The predictive analysis step thus controls whether or not to switch from one mode of coding to another. As is explained in more detail below, in a preferred embodiment, the six last data points are used to determine the most efficient coding mode to be used. Advantageously, the recent data can be temporarily stored in a data buffer prior to coding such that coding occurs using the most efficient coding mode selected (.i.e., which yields the fewest number of bits to code the data) by the predictive analysis.

In a preferred embodiment, the compression stage (g) comprises: (g1) in case of a change of coding mode, the creation of a "change of mode" code, and (g2) the creation of a data code representative of the value of the current sample, starting from the present value corresponding to the first derivative or the second derivative. Generally, after the stage (g), it is anticipated also to have a stage (h) of sequential memorization of the codes created in stages (g1) and (g2).

In addition, according to a certain number of preferred embodiments, other characteristics of the invention include:

it is anticipated in addition a stage (b) between the operation of the stages (a) and (c), of elimination of interferences due to the frequency of the power supply by pre-treatment (preprocessing) of the sensed sampled signal;

at the stage (c), the first derivative is obtained by determining the increment between (i) the current sampled signal acquired at stage (a) and (ii) a re-calculated value corresponding to the preceding sampled signal which is compressed at stage (g) and then decompressed by implementation of inverse coding, executed in a concurrent manner;

it is anticipated in addition a stage (d) between the stages (c) and (e), of possible reduction, by a given factor, of the resolution of the sampled signal, this factor being determined by comparison between an average speed of the current flow of data and a nominal control speed, such that the factor of reduction is increased when the average speed is greater than the nominal speed, and conversely.

Preferably, the plurality of coding modes includes one or more of the following:

a first coding mode in which the actual value of the second derivative of the sample signal is coded (memorized and preferably stored) as a variable length word and attributing a different length code word for each possible value of the second derivative, which first coding mode is preferably selected when the absolute value of the second derivative of the sampled signal is less than a first predetermined limit;

a second coding mode in which the actual value of the second derivative of the sampled signal is coded (memorized and preferably stored) as a code word of fixed length, which second coding mode is preferably selected when the absolute value of the second derivative of the sampled signal is greater than a second predetermined limit and less than a third predetermined limit; and a third coding mode in which the actual value of the first derivative of the sampled signal is coded (memorized and preferably stored) as either a code word of fixed length or a code word selected as the result of a logarithmic conversion of the value, which third coding mode is preferably selected when the absolute value of the second derivative of the sampled signal is greater than a fourth predetermined limit.

Preferably, the first and second predetermined limits are the same, and the third and fourth predetermined limits are the same, to provide three contiguous ranges.

In a particularly advantageous implementation, one also records at regular intervals, a table of states. The table preferably includes the following parameters: the present value of the first derivative; the currently selected coding mode; and the position in the recording (i.e., the static memory position or address) of the present memorized data (i.e., the location of the code word).

The invention also concerns a process of decompressing data that was compressed and memorized (and preferably stored) according to a compression process such as described above. The decompression is characterized by the successive steps of reading the individual memorized data, determining the coding mode written for the read data, and decompressing the memorized data by the inverse of the coding mode used in the compression.

The present invention also is directed to an apparatus operable to perform the aforementioned data compression (and decompression) for storage, transmission and display of the physiological data. Such apparatus is also usable in implanted devices, including without limitation Holter recording devices, and external and ambulatory Holter recording devices.

BRIEF DESCRIPTION OF THE DRAWINGS

Others characteristics, advantages and benefits of the invention will appear in view of the following detailed description of a preferred embodiment of the invention, with reference to the annexed drawings in which.

DETAILED DESCRIPTION OF THE INVENTION

Figure 1:
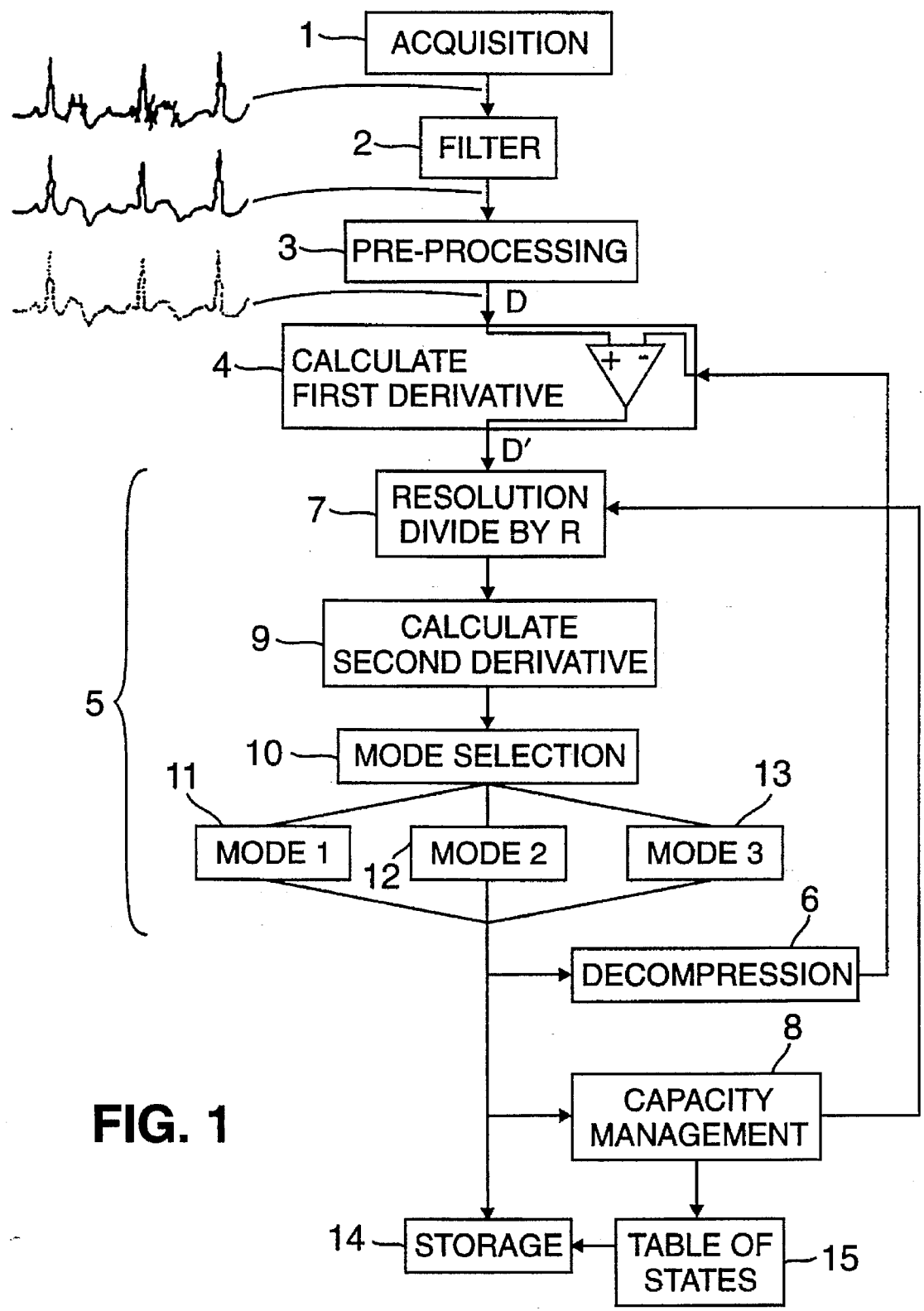
FIG. 1 illustrates a general flow chart of the process of compression according to a preferred embodiment of the present invention.

FIG. 1 gives, in a schematic manner, a sequence of the different stages of a process of compression in accordance with the present invention. Essentially, in the process of the invention, one has a plurality of different compression modes and one selects them automatically, in an adaptive manner, according to the content of the signal already collected. The process optionally includes, in an advantageous manner, an adjustment of the resolution, here again in an automatic and adaptive manner, allowing to modify the speed of data input to the memory as a function of the storage capacities of the system.

Acquisition and pre-treatment of ECG data

At stage 1, one proceeds first of all to the acquisition of data. Typically, this includes obtaining electronic signals of the ECG activity which are usually sensed in analog form, and converting the analog signals to digital sample values at a selected digitizing rate. The frequency of sampling can be chosen according to the desired quality of the signal and capacities of the compression algorithm, and according to the ability of an interference filter section, if one is used, to suppress interference signals. The term "sampled signal" as used herein is used synonymously with the terms "digital sample value," and "data point". The word "current" preceding any of the foregoing terms refers to a given data point under consideration for coding, as will be explained below.

The interference filtering section is realized at stage 2. If one supposes that the ECG signal has parasitic signals that are sinusoidal at a power line frequency of 50 Hz (60 Hz in the USA), it is possible to achieve a digital filtering of these parasites, which is very economic in time of calculation, of these parasites by averaging (a sliding average) four data points, all offset by 90°, that is to say to 5 ms apart (for a frequency of sampling=4×frequency of the main power at 50 Hz): this average yields a residual value that no longer contains the 50 Hz signal component. It is equally possible to filter 50 Hz interference signals by summing two spaced data points from a given central data point: being 180° out of phase to this frequency, these two values cancel. The bandwidth of the filter can be improved by giving coefficients optimized to data points that surround them. One thus obtains a clean signal, cleared of the main power interference signal, of sufficient signal quality for recording the ECG.

Further, in addition to filtering the main power, the filter section at step 2 also can provide a low pass filtering, with a cut-off frequency on the order 25 to 30 Hz, possibly commutable (switchable) to a higher frequency, 60 Hz for example, if one wishes to analyze micro-variations, but by accepting then, if need be, a higher level of parasitic signals. One can even anticipate, in the case of a signal that is practically free of parasites, to suppress all filtering by an appropriate switching of the filter 2. At stage 3, the process chooses a particular functioning of the data recording speed (which also depends on the size of the available mass memory space) from one of the following:

420 bits/second: one subsamples a data point every 10 ms, this point being the averaged four data points sampled at 200 Hz. If the original signal has few artifacts and there remains a surplus of memory, one takes the average of two data points spaced from a data point (to which one adds eventually the sum from the intermediate data point plus the preceding data point multiplied by a coefficient of −0.1 approximately, to increase the bandwidth).

900 bits/second: if the signal is little noisy, one samples at 200 data points per second. If the signal is slightly hummed or there is not a surplus of memory, then one reduces the noise by filtering on the two data points 180° apart, as described previously.

One thus obtains an output signal of data points, noted as D, representative of the ECG signal after implementation of the different preliminary processings (pre-treatment).

At stage 4, the first derivative of this sampled signal D is calculated, noted as D'. The term "first derivative" refers to the value of the increase of the signal between two successive data points. Indeed, since the ECG signal does not contain continuous components, the fact of saving only the first derivative does not imply any loss of information. On the other hand, with the sampling interval being constant, the increase of the value of the signal always varies in the same manner that the rate of increase of this same value, with the result that it suffices, by convenience, to consider simply the incremental variation of the signal from one sampling data point to the next.

In the same manner, one will call a "second derivative", noted as D", the increase of the first derivative (in the sense understood above) from one sampling data point to the next.

At stage 4, the calculation of the first derivative D' is undertaken by a determination of the difference between the value of the signal at the current data point and the corresponding value of this same signal at the preceding data point. The signal from the current data point to consider is, in any case, that delivered after any pre-treatment of stages 1 to 3 as already described. Concerning the preceding data point, due to the fact that the system, in the ulterior compression, can in some cases introduce a slight error in the value of the derivative after compression, one prefers, in stage 3, to determine a difference between the data from the current data point and the data from a reconstituted preceding data point. The reconstituted preceding data point is one that has first undergone a compression (following the sequence of one of the various referenced stages 5 as illustrated in the flow chart of FIG. 1) and then an inverse compression or a decompression (stage 6 on the figure). The possible error is thus not accumulated, because it will be compensated for in the following sampling. In one embodiment, instead of proceeding to a decompression, it is possible to obtain by calculating the data from the reconstituted preceding data point, by knowing the mode of selected compression and the value of derivative from the preceding data point.

Once the value of the first derivative D' is determined, and prior to proceeding to the actual compression, as an optional step, it is advantageously preferred to undergo an adaptive adjustment of the resolution of the signal acquired as shown at stage 7.

Indeed, one can often tolerate that an ECG signal is reproduced with a certain distortion, which allows of course to improve the accuracy of the algorithm of compression. But the major risk of the distortion is to create visible defects when the therapist observes the reconstituted signal on a display. It is especially indispensable, to avoid all reading and diagnosis error, to ensure that the process does not distort small waves or weak amplitude undulations, as exist, for example, with P waves of the atria, whose pertinence is very great for some pathologies.

If, conversely, one retains a lot of information, it will not be possible to compress sufficiently the acquired data and, accordingly, more of the parasitic signal. As it is absolutely necessary to limit the speed of data delivered to the mass memory, the process has to anticipate a means of reducing the speed for the storage of large volumes of information, but by reducing the speed by the smallest amount possible to preserve the quality of the recording.

A compromise therefore has to be made in a case by case situation. To obtain such a compromise, the invention proposes to act in an adaptive manner for controlling the resolution of the acquired signal, which operation is realized at stage 7. Practical experience has shown that it is more preferable to vary the resolution of the ECG signals rather than to operate, for example, a low pass filtering of the signal, such that a low resolution signal, in which the parasitic signals do appear, occurs infrequently in practice.

The choice of the resolution is based on an analysis of the remaining capacity of the mass memory. The analysis is undertaken by a capacity management module (at stage 8). The criterion includes determining if, considering the volume of information already memorized and stored since the beginning of the signal acquisition (i.e., the time period of acquisition), the rate of data acquisition is found to be ahead of or behind the average control speed. The average real speed value is calculated, for example, by dividing the volume of information stored in the mass memory (size of the file) since the beginning of the acquisition, by the number of elapsed seconds since the volume was measured. This average real speed is compared to an average control speed, which is calculated in this example as the total file space in the memory (i.e., storage capacity) divided by the number of seconds of a complete recording, e.g., the number of seconds in 24 or 48 hours.

If the average real speed is greater than the control speed, which means that it is "ahead" and that, at this rate, the memory will be totally filled before the end of the 24 or 48 hour period, then the resolution is reduced to, e.g., a half, a third, a quarter, etc., of the base resolution (division by R=2, 3, 4, etc.). The factor R of reduction of the resolution is chosen, for example, to be greater if the gap between the average real speed and the control speed is large, so as to return the real speed more rapidly to near the control speed. Conversely, if the real speed is "behind" the control speed, which means that, in the present condition, the memory would be only partially used at the end of 24 or 48 hours, then the value of R is decreased so as to return to obtaining more detailed data (increase the resolution) to occupy the memory more completely.

A reduction of the resolution has for an effect an immediate reduction of the flow of compressed information, due to the disappearance of all small waves and the reduction of the dynamics of the derivative values (the process compressing all the more efficiently that these values are small, as explained hereafter). The risk in this case of the loss of the small waves is then without great importance, the former being most often drowned in artifacts (a more detailed (resolved) signal almost always contains the artifacts).

The best value of resolution (R=1) corresponds for example to 10 μV, and can be used when one is found in the best possible conditions. For the signals containing parasitic signals, one can increase this value by increments of 10 μV until 40 μV (R=4), a value compatible with typical parasite levels, which are on the order 5 to 10 μV in the majority of situations met in practice.

In addition, although one has reduced the resolution, this figure of 40 μV is comparable to the typical resolution of classic machines, which have a fixed resolution on the order 50 μV. The invention obtains therefore, even in a "degraded mode", that is to say with the level of lowest (worst) resolution, an improvement in resolution as compared to the prior art devices.

One will note that stage 7 of adaptive reduction of the resolution is advantageously placed after stage 4 of calculation of the first derivative. Thus, a change of resolution produces no discontinuity in the signal, while it would have produced a discontinuity in the reverse case, as soon as the data would not have been equal to zero. One thus avoids accumulating errors produced by changes in resolution.

The next stage, that is stage 9, is a stage of calculation of the second derivative (calculation of the difference between the first derivative from the current data point and the first derivative from the preceding data point). This datum is used in certain of the compression modes.

The compression process then passes then to the compression sequence proper (stages 10 to 13).

Pre-treated data compression

In a characteristic manner, the system chooses between one of several compression modes, also called a "coding mode" in that a code word is used in place of the actual value of the data point. With reference to FIG. 1, the system is chosen, for example, among three modes 11, 12 and 13. The selection is made according to the first derivative value D' and the second derivative value D" related to each current data point being considered. This general principle permits recording one or more bits for each current data point—the most frequent and longer portions of an ECG waveform—corresponding to a second derivative that is stable enough (almost a flat segment or a regular slope), and a number of more significant bits (for example 7 bits) in response to a large slope or large variability. The system can toggle at any given time from one compression mode to another by sending a mode change code. The compression algorithm is to be sufficiently predictive to optimize the number of changes of mode per second, these codes coming indeed to be added to information by reducing the so-called global score. In other words, by knowing in advance, for example, three or four second and first derivative values, one evaluates the global score of the compression with or without a change of mode and determines whether or not to select another mode according to this evaluation. This predictive analysis is discussed following the discussion of the illustrated example, in which the selection of a coding mode is among three modes 11, 12 or 13. However, one can, without exiting the framework of the invention, envisage a system simplified to a choice of two coding modes, or a system having more than three coding modes. These variations will be discussed further below.

In the illustrated implementation, the three types of coding are as follows:

mode no. 1: coding of the second derivative as a variable length code word; this first mode, corresponding to the low value of the derivative, is well adapted to slow waves, i.e., waves that vary slowly over time, which constitute a great part of the ECG signal;

mode no. 2: coding of the second derivative as a permanent length code word; this second mode is well adapted to average values of first derivative; and mode no. 3: coding of the first derivative as a permanent length code word; this third mode is well adapted to rapid waves or to brutal amplitude variations of the ECG signal (for example, large P waves).

Coding Mode No. 1

The coding according to mode no. 1 (stage 11) is, for example, selected for use when the second derivative value remains between +2 and −2 units (that is ±20 mV, if the unit is 10 mV). The chosen program then stores the value of the second derivative by allocating a variable length word for each possible value in the range. This is the principle of Huffmann coding. In as much as, statistically, the value 0 is the most frequent value, one attributes the smallest binary word, a word of 1 bit (for example the value "0") to this value; the values +1 and −1 are then typically the next most frequent values, and one attributes the next smallest binary value "10" to +1, and the binary value "110" to −1; and finally, for +2 and −2, one attributes binary values "1110" and "11110" respectively.

In others words, the second derivative value is coded by use of a "dictionary" or look-up table correlating each of a range of possible second derivatives values to a code in binary words, preferably a unique code for each possible data value, so long as the value of the second derivative is known to be within a first predetermined limit between −2 and +2. As soon as this limit range is exceeded, it is necessary to change the mode of coding. The change of mode is for example indicated by a unique code of "11111".

One obtains thus the following coding table (it should be understood that the choice of bits 0 or 1 can be inverted, and the attribution of the sign + or − is arbitrary):

| D" | Data Code |
|---|---|
| 0 | 0 |
| +1 | 10 |
| −1 | 110 |
| +2 | 1110 |
| −2 | 11110 |
| ID"I>2 | 11111 |

Coding mode No. 2

The coding mode no. 2, implemented at stage 12, is used whenever the second derivative value exceeds the first predetermined limit of ±2, and remains within a second predetermined limit ±7. In this mode the second derivative value is stored in the form of a fixed length code word of 4 bits. A specific code, for example, the code −8 ("1000" in binary form) allows exiting this second coding mode, such that the code −8 is followed by a bit 0 to pass again to coding mode no. 1 (e.g., the case that the second derivative value stabilizes to low values), or by a bit 1 to pass to the coding mode no. 3 (in the case that the second derivative value exceeds the limit of ±7). One thus obtains the following table of coding:

| D" | Data Code |
|---|---|
| 0 | 0000 |
| +1 | 0001 |
| ... | ... |
| +7 | 0111 |
| −1 | 1111 |
| ... | ... |
| −7 | 1001 |
| ID"I>7 passage to mode no. 3: | 1000 +1 |
| ID"I<2 return to mode no. 1: | 1000 +0 |

One will note that the coding allowed by mode no. 2 covers that permitted by mode no. 1. There is a redundancy for values 0, ±1 and ±2. This is done to avoid frequent switchings of mode, that would unnecessarily raise the global score of the compression algorithm.

The decision to change the mode or maintain in the same mode is taken at stage 10, briefly described above and further below, that is, as one has indicated it in a predictive analysis stage of the global score, allowing one to optimize the number of changes of modes per second.

Coding mode No. 3

The coding mode no. 3 is implemented at stage 13. For large values of the second derivative, that is values beyond the second predetermined limit of ±7, instead of coding the second derivative, one directly codes the first derivative.

First derivative values are preferably stored as words of 7 bits, which corresponds to a dynamic range of ±63. Preferably, the first derivative values are converted by the intermediary of a predetermined logarithmic correspondence (look-up) table preserved in memory, allowing, by a known manner, a greater input dynamic range of, e.g., ±200 to correspond to an output dynamic range of ±63. The error introduced by such a conversion is negligible or zero for small values (the logarithmic conversion being, for example, undertaken without any significant change of values until ±12), then increases gradually with values themselves, while always remaining below 10%. In any case, since one directly codes the first derivative, this error does not accumulate from one data point to another and does not create therefore, a perceptible deformation on the ECG trace.

One obtains the following table of coding:

| D' | Data Code |
|---|---|
| 0 | 0000000 |
| +1 | 0000001 |
| ... | ... |
| 62 | 0111110 |
| 63 pass to the resolution R: | 0111111 + R |
| 64 return to mode no. 2: | 1000000 |

The code 64 has been reserved to correspond to a control value to return to mode no. 2 when the second derivative stabilizes to a value that is less than ±7. One will note that, to exit the mode no. 3, one has to have recorded a first derivative without error. Indeed, as mode no. 2 (and similarly the mode no. 1) records only the second derivative, it has to be possible to re-compute during the decompression the first derivative from a correct value to avoid all drift.

Another code is reserved. It concerns, for example, code 63, which serves to introduce a change of resolution (divide by R at stage 7). In the preferred embodiment, the change of resolution occurs only when the system is in coding mode no. 3. If the memory capacity management module (stage 8, described above) decides to modify the resolution, the routine waits to be in mode no. 3 to proceed with the adjustment. However, if the mode no. 3 does not occur after a given time lapse (for example, in the case of a slow signal after a parasite), then the algorithm can force the momentary passage to mode no. 3 to introduce in the memory the specific code to change the resolution.

The predictive analysis of the global code score concerns minimizing the number of bits stored based on recent data points. In one embodiment, this step evaluates a given number of data points, more preferably six or eight of the first derivative values, which are temporarily stored in a buffer, and determines the number of bits required to code those values in the different possible coding modes, taking into account the number of consecutive values that can be coded in a more bit efficient coding mode and the number of bits of any change of mode code that might be required. The analysis step then selects the coding mode that produces the fewest number of bits, and codes the group of data points using the selected coding mode. Any necessary change of coding mode codes also is included.

The use of the last number of data points (or the first derivative values) is preferably made on a batch basis. Thus, for example, nine data points at a time are evaluated, such that eight first derivative and seven second derivative values are calculated, and the nine data points are then coded according to the selected coding mode or modes. Then the next group of nine data points are acquired and analyzed. Alternatively, the data points may be analyzed on a sliding window basis (in the manner of a first-in first-out stack memory) such that a given data point might be first coded using one mode based on a first group of nine data points including the given data point, and then recoded using a different coding mode based on a second group of nine data points including the given data point.

In one embodiment, the analysis step also examines whether there are some number of consecutive second derivative values, e.g., three, within the given group of data points, that have the same value that can be more efficiently coded in a different coding mode than the other data points in the group. This analysis takes into consideration the number of bits needed to record one (or two) change of mode codes. Consequently, it may be more efficient to change the mode within the same group of data points than to keep the same coding mode for the given group. Thus, the more efficient coding mode or modes is used.

In yet another embodiment, a pattern analysis may be used to determine how to code a given number of data points. Thus, if the pattern of second derivative values and the coding modes available to code those values includes, for example, three consecutive values in mode 2, two consecutive values in mode 1 or mode 2, followed by two consecutive values in mode 2, the pattern analysis will produce a result that says to code all of the data in mode 2 because it will likely be more efficient. This is further illustrated in the Table and discussion below. Other patterns can be empirically determined and used to evaluate acquired data (i.e., the second derivative values) to facilitate the predictive analysis and efficient coding.

An application of the invention is shown in the following Table, which presents the eight first derivative values D' and seven second derivative values D" calculated from a group of nine data points, the available coding modes for the second derivative values, the number of bits needed to code the values, and the number of bits in any applicable mode change code, as follows:

TABLE

| D' | D" | Coding Mode | Mode 2 | Mode1 | Change Mode Code |
|---|---|---|---|---|---|
| 0 | 6 | 2 | 4 bits | — | |
| 6 | −1 | 1 or 2 | 4 bits | 3 bits | |
| 5 | 6 | 2 | 4 bits | — | + 5 bits |
| −1 | −1 | 1 or 2 | 4 bits | 3 bits | |
| −2 | +2 | 1 or 2 | 4 bits | 4 bits | + 5 bits |
| −0 | −6 | 2 | 4 bits | — | |
| −5 | −1 | 1 or 2 | 4 bits | 3 bits | |
| −6 | | | | | |

From the above Table, it is apparent that if the entire set is coded in mode 2, 28 bits are required (7×4). If, however, the two consecutive second derivatives that can be coded in mode 1 are coded that way, then a total of 37 bits are required (five terms in mode 2 at four bits each, two change of mode codes at 5 bits each, and two terms coded in mode 1 at three and four bits respectively). Thus, the predictive analysis routine compares these totals and produces a result that says to code all of the data in mode 2 as more efficient. Similarly, applying a predetermined pattern of 3 mode 2:2 mode 1:2 mode 2, based on consecutive coding modes available, can produce the same result without having to count bits or compare the total bits counted using two or more different coding modes. It is to be understood that multiple patterns can be applied to the same set of data to obtain a result, such that if one pattern indicates a more efficient coding mode combination, that coding mode combination will be used.

It is noted that in the case that the number of changes of mode within a given group which can be tolerated will change depending on the size of the data group being analyzed, and the selected number of consecutive values within a group that are used. The consecutive number of data points in a group is selected to avoid frequent switching such that the net bit count, taking into consideration the number of bits used in a change of coding mode code, will result in some savings.

In the context of the three coding modes discussed, the predictive analysis step is particularly advantageously implemented when the data point in the given coding mode has a value in a range overlapped by more than one coding mode. Thus, if the analysis of the last number data points places the system in mode 2, and there are three consecutive data points in that group in which the value of the second derivatives is ≦±2, such that it also could be coded in mode 1, the predictive analysis step will consider whether or not it is more efficient to switch to mode 1 for three successive values of ≦±2 and be in mode 2 for the other data points. As illustrated above, two consecutive second derivative values did not result in greater efficiency using mode 1. Also as noted above, using a pattern recognition technique will simplify and facilitate the coding process. In this way, the global code score of the memory is minimized. Importantly, this also permits increasing the resolution of the data acquisition and providing an overall improved data compression system. It is noted that the change from mode 1 to mode 2 and mode 2 to mode 3 will automatically happen when the data point second derivative value exceeds the range limit, whereas the predictive analysis step is used to reduce the code size when series of data points can be coded in a more bit efficient manner, including changing between one or more coding modes with minimal mode switching. This is particularly useful for improving the bit efficiency after the transients of a P wave or an R wave of the ECG when the ECG signal is relatively stable. The predictive analysis may be implemented using a counter (memory) which keeps track of the consecutive numbers of data point (second derivative) values, such that the decision whether or not to switch the coding mode within a given group of data points (or a pattern analysis) is made when the counter reaches a preset limit. The person of skill in the art will understand that the code bit sizes and numbers of values in a group or consecutive data points in a group may be selected as a matter of design choice.

Memorization

The sampled signal data is thus coded by one or the other of these compression modes. The codes are placed end to end in bytes or words of the Holter memory (stage 14 of storage). One will notice that, due to the fact that the data does not have a permanent or uniform fixed length, a boundary of data does not necessarily correspond to a byte or word boundary of the memory.

Decompression

The decompression operates by rereading in a sequential manner compressed data (i.e., the codes) and by processing each code using an inverse coding according to the mode of coding used to compress the data (mode no. 1, 2 or 3). Thus, if data is found coded in mode no. 1, the algorithm reads stored bits until it finds a '0' followed by a repetition of five '1's. In this last case, the decompression algorithm passes to the mode no. 2 and reads the sequence of data in groups (blocks) of four successive bits, without particular difficulty because the coding is fixed length in this mode. In the case of codes coded in mode no. 3, one proceeds in the same manner, but using blocks of 7 bits to read the sequence.

In modes no. 1 and no. 2, after having thus found the second derivative value, one integrates it to obtain the first derivative. In the mode no. 3, the first derivative value is written directly (or recovered after inverse conversion according to the logarithmic table, if used). Then, the integration of the first derivative value gives the amplitude of the real signal, which then can be displayed on a screen, stored in a data memory, traced (printed) on a strip recorder etc., to allow its interpretation by the therapist (medical practitioner).

It should be understood, however, that the decompression thus realized need not be performed only sequentially.

A first possibility, the simplest, is to perform a decompression of the complete file, from the beginning until the end. Despite the rapidity of the decompression (typically 400 to 500 times faster than real time with the computers currently used in these applications), the preliminary operation can take several minutes, which can be annoying when one wishes be able to explore rapidly the signal, notably when interesting parts of the signal occur near to the end of the 24 or 48 hour recording period.

Thus, to allow a more rapid access to a sample of ECG situated anywhere in the recording, one can advantageously, simultaneously to the compression, record periodically a table of states (at stage 15 of FIG. 1) of the acquired information. For example, the table of states could include a recording, at each minute or at some other regular interval, an entry for one or more of the instantaneous states of the system: the current coding mode (no. 1, 2 or 3), the resolution (value of the factor R), position of the next memory address in the file (necessary when a word or byte border of the file does not correspond to a boundary of the recording), and the value of the first derivative. When one wishes to proceed, at the moment of the end of the recording, to review or read a particular portion of this recording, it suffices to search in the table of states for the data corresponding to the minute preceding the chosen instant, and to undertake the decompression of data from this position in the memory forward, and hence not from the beginning of the memory, as in the preceding case. One thus arrives practically in an instantaneous manner to the sought-after point, which allows to be displayed without delay the sample of ECG desired by the therapist.

The state table can of course be organized other than minute by minute, but there is some practical restraint to have an interval of some seconds or minutes in the table of states in order not to occupy too much memory volume and to maintain sufficient memory performance to be effective.

In a possible variation of the invention, this table of states is not constructed in real time at the moment of the recording of data in the Holter memory, but rather, in differential time during a first reading of the data, and executed integrally. This allows one to preserve the data in the memory in the computer of the therapist in a compressed form, with a correlative space gain.

Implementation Variations

The compression process of the present invention is not limited to the three modes (mode no. 1, 2 and 3 described above).

It is possible to use, for example, a simplified process having only two modes, mode no. 1 and no. 3, for example. Conversely, it is possible to improve the process with a system of N modes (N >3). By thus generalizing the process, one can optimize the size of words stored in memory as a function of the incoming data. In this regard, the system maintains always a principle of coding the second derivative for modes no. 1 to N−1, and coding the first derivative for the mode N, at the highest level. More precisely, one calculates from a number of given data points, that is to say to a "horizon" that can be variable, negative and positive maximal values that take the second derivative and the first derivative. According to the maxima, one selects a size of a given data word (for example 1 bit for successive zeroes, 2 bits for −1, 0, +1), the extreme negative value serving to exit the currently used mode, this extreme negative value being immediately followed by a word 3 bits defining the level of the following mode: no. 1 for 1 bit, no. 2 for 2 bits, . . . , no. 7 for 7 bits (corresponding to a first derivative coding by the intermediary of a logarithmic conversion table). The zero word is, as for it, reserved to introduce changes of resolution, that take place in the same manner and with the same constraints that is described in the process of the three modes described above.

Figure 2:
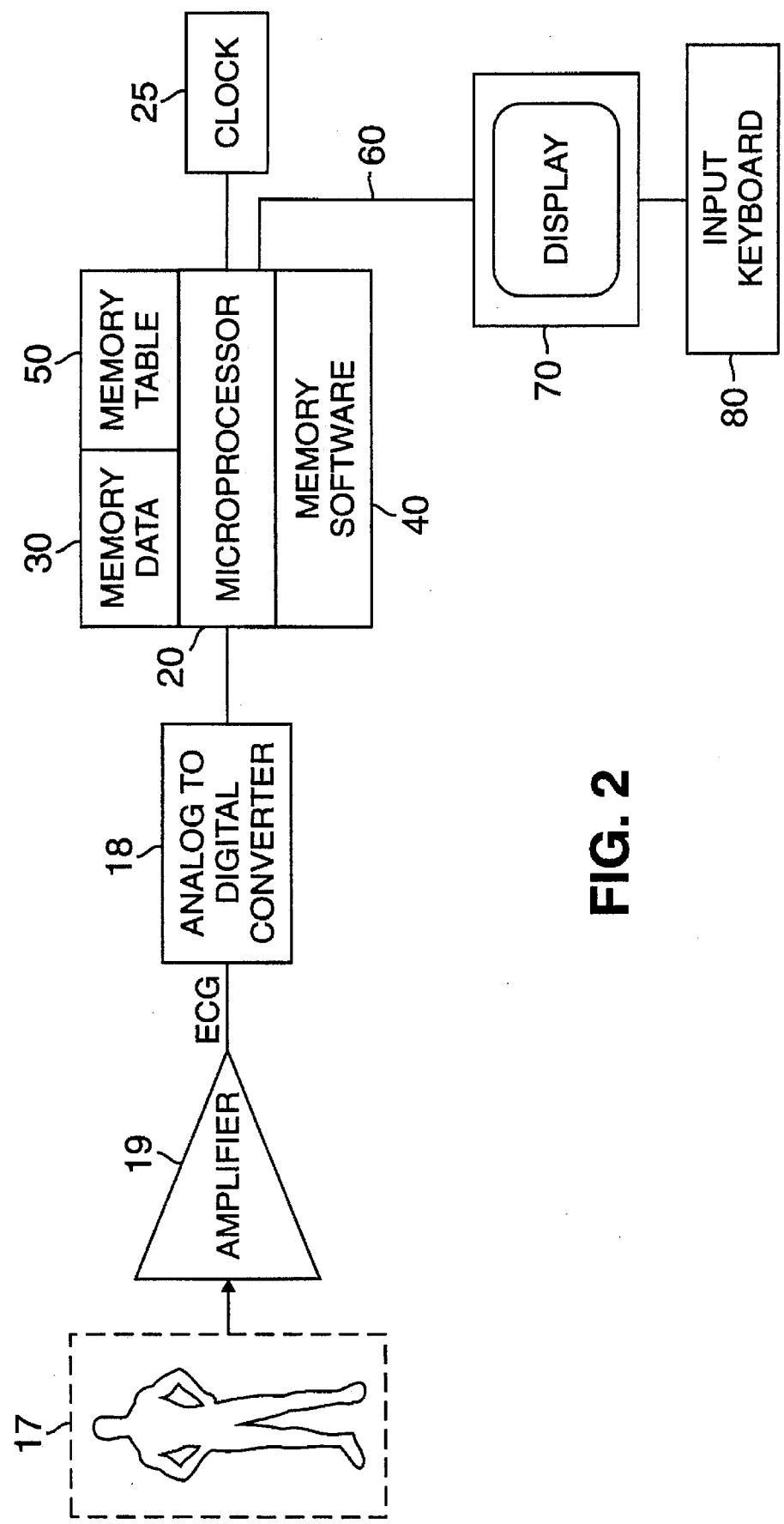
FIG. 2 is a schematic block diagram of an apparatus in accordance with a preferred embodiment of the invention.

With reference to FIG. 2, the detection of an ECG signal is schematically shown by obtaining sensed electrical cardiac activity signals of a person 17, which may be by use of external leads (or internal leads sensing an electrogram, as in the case of implanted medical devices such as pacemakers, cardioverters, and defibrillators which have Holter recording functionality). The signal sensing is performed in a conventional manner and does not itself form any part of the present invention. The apparatus used to obtain the Holter data also are known and thus do not form any part of the present invention, except to the extent they need to be modified as disclosed herein to operate in accordance with the present invention.

The apparatus in accordance with the present invention thus includes an amplifier 19, an analog to digital converter 18 to convert the analog ECG signal to a digital form, e.g., at a selected sampling rate, e.g., 100 or 200 samples (data points) per second, a microprocessor 20 having static memory 30 for storing compressed data in the form of the aforementioned codes (or direct binary values of the first derivative when so used), memory space 40 for storing suitable software operable to execute the compression and decompression processes as described above, and optionally memory space 50 for storing a table of states of the compressed data to enable the therapist to review rapidly selected portions of the data, as described above. A clock 25 is shown as illustrative of a device used for counting the various time intervals for recording ECG data over the conventional 24 or 48 hour periods used in Holter recording, as well as other clock functions that are conventional in a microprocessor controlled device.

It is deemed within the abilities of a person of ordinary skill in the art to develop software suitable for performing the data compression process of the present invention, and in particular such as that shown in the flow chart of FIG. 1. Also, the selection of the number of coding modes, the predetermined limits for changing the coding modes, and the lengths of the fixed lengths words to be used in the coding, and the number of states and recording interval to be used in a Table of States (when used), are deemed to be design choices that may be varied to suit the particular circumstances and the memory capacity of the devices being used. In this regard, although illustrated as three devices, memories 30, 40 and 50 may comprise one or more discrete devices, or separate areas of a common device.

Also illustrated in FIG. 2 are the conventional elements of an output communication link 60, a display device 70 on which decompressed data may be viewed by the therapist, and an input device 80 so that the therapist can control the ECG signals to be displayed. The input device such as a keyboard, touch screen or the like, also may itself be a part of a computing system having a separate central processing unit and memory devices.

In the context of an implanted device, the communication link 60 may be a conventional telemetry link to an external programmer, the latter of which includes display 70 and input device 80. Such implanted devices may be, for example, a rate adaptive pulse stimulator device sold under the OPUS or CHORUS trade names, and an implantable defibrillator sold under the trade name DEFENDER, all of which are available from ELA Medical, Montrouge FRANCE. These devices include both ROM memory, in which software for operating the process of the present invention may be embedded, and RAM memory for operating on the acquired electrogram information by the algorithm and for storage of the compressed data (codes), the Table of States, and optionally, the software and/or programmable parameters for configuring the software to perform the compression and decompression procedures.

It should also be understood that the present invention is applicable to converting real time recordings of Holter data, as are conventionally recorded on magnetic tapes using external devices, into a compressed form for archival and rapid retrieval in a static memory. Such an external monitoring device, which includes a commercial embodiment of the present invention and uses a 24 hour recording period, is sold under the trade name SYNESIS, which is available from ELA Medical. The SYNESIS device uses a flash memory device as a type of reprogrammable read only memory device for the static Holter memory as well as other RAM functions.

One skilled in the art will appreciate that the present invention can be practiced by other than the described embodiments which are presented for purposes of illustration and not of limitation.

I claim:

1. A process for physiological data compression, comprising the steps of:
   a) acquiring an electrical signal having an amplitude variation representative of the physiological data to be compressed during a given time period;
   b) sampling the acquired electrical signal amplitude at a predetermined frequency;
   c) processing the sampled signals by:
      i) determining a first derivative of a current sampled signal;
      ii) determining a second derivative of the current sampled signal;
      iii) performing a predictive analysis of the current sampled signal amplitude as a function of a plurality of values of the first and second derivatives;
      iv) selecting a coding mode from among at least two coding modes as a function of the predictive analysis to optimize a global volume of a memory in which to store compressed physiological data for the given time period, said coding modes being dynamically switchable from one mode to another mode; and
   d) compressing the sampled signal by implementing the selected coding mode.

2. The process of claim 1, in which step c) further comprises providing a change of mode code in response to a change of coding mode in step c) iv); and step d) further comprises providing a data code representative of the value of the current sampled signal as a function of the corresponding value of one of the first or second derivative values of the current sampled signal; the process further comprising the step of:
   e) storing sequentially in a memory said change of mode code and said data codes.

3. The process of claim 1, further comprising prior to step c) i) the steps of pre-processing the sampled signals and minimizing interference attributable to a power-line frequency in said electrical signal.

4. The process of claim 3 wherein the pre-processing step further comprises pre-processing a sequence of sampled signals.

5. The process of claim 1, wherein step c) i) further comprises:
   recalculating a prior sampled signal value by obtaining a compressed sampled signal corresponding to said prior signal sample amplitude after compression, and decompressing said compressed sampled signal by the inverse of the current coding mode; and determining an increment between the current sampled signal and the recalculated prior sampled signal.

6. The process of claim 1, further comprising:
   e) storing said compressed sampled signal in a memory; wherein step d) provides data compression with a variable resolution, further comprising the steps f1)–f4), interposed between steps c) i) and c) ii), of:
      f1) determining an average speed of flow of data being stored in step e);
      f2) determining a factor of resolution by comparing the average current speed relative to a predetermined control speed;
      f3) increasing the factor R when the average speed is greater than the control speed and decreasing the factor R when the average speed is less than the control speed; and
      f4) adjusting the resolution of the sampled signal by the factor R.

7. The process of claim 1, further comprising a step of providing a plurality of coding modes of which at least one coding mode comprises the steps of:
   assigning a code word of variable length to each of a first range of possible values of the second derivative;
   selecting the variable length code word corresponding to the value of the second derivative of the current sampled signal; and
   storing said selected variable length code word in a memory as the compressed sampled signal.

8. The process of claim 7, further comprising selecting the one coding mode in response to the absolute value of the second derivative of the current sample signal being less than a first predetermined limit defining the first range.

9. The process of claim 1, further comprising a step of providing a plurality of coding modes of which at least one coding mode comprises:
   assigning a code word of fixed length to each of a first range of possible values of the second derivative;
   selecting the fixed length code word corresponding to the value of the second derivative of the current sampled signal; and
   storing said selected fixed length code words in a memory as the compressed sampled signal.

10. The process of claim 9, further comprising selecting the one coding mode in response to the absolute value of the second derivative of the current sampled signal being greater than a first predetermined limit and less than a second predetermined limit defining the first range.

11. The process of claim 1, further comprising a step of providing a plurality of coding modes of which at least one coding mode comprises:
   assigning a code word of fixed length to each of a first range of possible values of the first derivative;

selecting the fixed length code word corresponding to the value of the first derivative of the current sampled signal; and storing said selected fixed length code word in a memory as the compressed sampled signal.

12. The process of claim 11, further comprising the step of selecting said one coding mode in response to the absolute value of the second derivative of the current sampled signal being greater than a predetermined limit.

13. The process of claim 1, further comprising a step of providing a plurality of coding modes of which at least one coding mode comprises:

providing a logarithmic conversion table relating a first range of values of the first derivative to a second range of fixed length code words;

determining a fixed length code word of corresponding to the value of the first derivative of the sampled signal according to said table; and storing said determined fixed length code word of in a memory as the compressed sampled signal.

14. The process of claim 13, further comprising the step of selecting said one coding mode in response to the absolute value of the second derivative second of the current sampled signal being greater than a predetermined limit.

15. The process of claim 1, further comprising recording a table of states at regular intervals in a memory, said table of states comprising:

the current value of the first derivative;

the current coding mode, and the position the current data is stored in memory.

16. A process of decompression of data compressed according to the method of claim 1, comprising the steps of:

reading and isolating said compressed sampled signal;

determining the current coding mode of the read compressed sampled signal; and decompressing the read compressed sampled signal by an inversion of the determined coding mode.

17. The process of claim 1 further comprising a step of providing first, second and third coding modes, wherein:

the first coding mode comprises:

assigning a code word of variable length to each of a first range of possible values of the second derivative;

selecting the variable length code word corresponding to the value of the second derivative of the current sampled signal; and storing said selected variable length code word in a memory as the compressed sampled signal; the second mode comprises:

assigning a code word of variable length to each of a second range of possible values of the second derivative;

selecting the variable length code word corresponding to the value of the second derivative of the current sampled signal; and storing said selected variable length code word in a memory as the compressed sampled signal; the third coding mode comprises:

assigning a code word of fixed length to each of a third range of possible values of the first derivative;

selecting the fixed length code word corresponding to the value of the first derivative of the current sampled signal;

storing said selected fixed length code word in a memory as the compressed sampled signal; and wherein step c) iv) further comprises:

selecting the first coding mode in response to the absolute value of the second derivative of the current sample signal being less than a first predetermined limit;

selecting the second coding mode in response to the absolute value of the second derivative of the current sampled signal being greater than the first predetermined limit and less than a second predetermined limit; and selecting the third coding mode in response to the absolute value of the second derivative of the current sampled signal being greater than the second predetermined limit.

18. The process of claim 1 wherein step c) iii) further comprises analyzing a preselected number of sampled signals, and determining a first coding mode corresponding to one of the at least two coding modes which results in the smallest volume of compressed data and wherein step c) iv) further comprises selecting the determined first coding mode.

19. The process of claim 18 wherein step c) iii) further comprises analyzing said preselected number of sampled signals, determining when there is a second number of said sampled signals that could be coded in a smaller volume using a coding mode other than said determined first coding mode, and wherein step c) iv) further comprises selecting the other coding mode for compressing the data of said second number of sampled signals and selecting the determined first coding mode for compressing the data of the other of said first predetermined number of sampled signals.

20. An apparatus for recording Holter data in a compressed form comprising an input for electrical signals representative of an electrocardiogram, a static memory device, a microprocessor, and an analog to digital converter, the analog-to-digitial converter being operatively connected to said input for receiving said electrical signals and having a digital output corresponding to said sampled signals, wherein the microprocessor is operatively connected to the digital output and the static memory device and operable to process said sampled signals in accordance with the process of claim 1 and store the compressed sampled signals in the static memory.

21. An implantable medical device for recording Holter data in a compressed form comprising an input for electrical signals representative of an electrocardiogram, a static memory device, a microprocessor, and an analog to digital converter, the analog-to-digital converter being operatively connected to said input for receiving said electrical signals and having a digital output corresponding to said sampled signals, wherein the microprocessor is operatively connected to the digital output and the static memory device and operable to process said sampled signals in accordance with the process of claim 1 and store the compressed sampled signals in the static memory.

22. The apparatus of claim 21 further comprising a telemetry transmission link coupled to said microprocessor and operable to transmit the stored compressed sampled signals in said static memory to an external device.

* * * * *